United States Patent
Gerold et al.

(10) Patent No.: US 8,293,031 B2
(45) Date of Patent: *Oct. 23, 2012

(54) MAGNESIUM ALLOY AND THE RESPECTIVE MANUFACTURING METHOD

(75) Inventors: Bodo Gerold, Zellingen (DE); Heinz Mueller, Erlangen (DE); Joerg Loeffler, Zurich (CH); Anja Haenzi, Baden (CH); Peter Uggowitzer, Ottenbach (CH)

(73) Assignee: Biotronik VI Patent AG, Baar (CH)

( * ) Notice: Subject to any disclaimer, the term of this patent is extended or adjusted under 35 U.S.C. 154(b) by 743 days.

This patent is subject to a terminal disclaimer.

(21) Appl. No.: 11/829,665

(22) Filed: Jul. 27, 2007

(65) Prior Publication Data

US 2008/0031765 A1 Feb. 7, 2008

Related U.S. Application Data

(63) Continuation-in-part of application No. 11/691,754, filed on Mar. 27, 2007.

(30) Foreign Application Priority Data

Mar. 31, 2006 (DE) .......................... 10 2006 015 457

(51) Int. Cl.
*C22C 23/00* (2006.01)
*C22F 1/06* (2006.01)

(52) U.S. Cl. ........ 148/420; 148/666; 148/667; 420/402; 420/403; 420/404; 420/405; 420/406; 420/411; 420/412

(58) Field of Classification Search .................. 148/420, 148/666, 667; 420/402–406, 411–412
See application file for complete search history.

(56) References Cited

U.S. PATENT DOCUMENTS

| | | | |
|---|---|---|---|
| 3,334,998 A * | 8/1967 | Fisher | 420/405 |
| 3,419,385 A | 12/1968 | Foerster et al. | |
| 5,073,207 A * | 12/1991 | Faure et al. | 148/667 |
| 5,248,477 A | 9/1993 | Green et al. | |
| 2003/0183306 A1 | 10/2003 | Hehmann et al. | |
| 2006/0246107 A1 * | 11/2006 | Harder et al. | 424/426 |
| 2007/0258845 A1 * | 11/2007 | Kondoh | 420/405 |

FOREIGN PATENT DOCUMENTS

| | | | |
|---|---|---|---|
| AT | 251893 | | 1/1967 |
| DE | 1239105 | | 11/1967 |
| DE | 1248306 | | 3/1968 |
| DE | 1953241 | | 5/1971 |
| DE | 2658187 | | 6/1977 |
| DE | 19915277 | A1 | 10/2000 |
| EP | 0219628 | B1 | 5/1990 |
| EP | 0407964 | A2 | 1/1991 |
| EP | 0531165 | A1 | 3/1993 |
| EP | 1419793 | * | 5/2004 |
| GB | 1035260 | | 7/1966 |
| GB | 1067915 | * | 5/1967 |
| GB | 1075010 | | 7/1967 |
| GB | 1525759 | | 9/1978 |
| JP | 06316750 | * | 11/1994 |
| JP | 8134581 | | 5/1996 |
| JP | 9041065 | * | 2/1997 |
| JP | 2004099941 | | 4/2004 |
| JP | 2005213535 | A | 8/2005 |
| WO | 2005123972 | * | 12/2005 |

OTHER PUBLICATIONS

Hort et al.; Intermetallics in Magnesium Alloys; Advanced Engineering Materials; 2006; pp. 235-240; 8, No. 4.
Search Report for German Patent Application No. 10 2006 015 457.6; Mar. 31, 2006.

* cited by examiner

*Primary Examiner* — Sikyin Ip
(74) *Attorney, Agent, or Firm* — Greer, Burns & Crain, Ltd.

(57) ABSTRACT

A magnesium alloy, comprising:

| | |
|---|---|
| Y: | 0.5-10 |
| Zn: | 0.5-6 |
| Ca: | 0.05-1 |
| Mn: | 0-0.5 |
| Ag: | 0-1 |
| Ce: | 0-1 |
| Zr: | 0-1 or Si: 0-0.4, | wherein the amounts are based on weight-percent of the alloy and Mg, and manufacturing-related impurities constitute the remainder of the alloy to a total of 100 weight-percent. Also disclosed is a method for manufacturing such an alloy and a biodegradable implant formed therefrom.

13 Claims, No Drawings

MAGNESIUM ALLOY AND THE RESPECTIVE MANUFACTURING METHOD

CROSS REFERENCE TO RELATED APPLICATIONS

This patent application is a continuation-in-part of co-pending U.S. patent application Ser. No. 11/691,754, filed Mar. 27, 2007, entitled Magnesium Alloy and Associated Production Method, which claims priority to German Patent Application No. 10 2006 015 457.6, filed Mar. 31, 2006, the disclosures of which are incorporated herein by reference in their entirety.

FIELD

The present disclosure relates to a novel magnesium alloy and its use and a respective manufacturing method for the magnesium alloy.

BACKGROUND

Numerous magnesium alloys having a wide variety of compositions and uses are known. For purposes of the present disclosure, the term "magnesium alloy" is understood to refer to a group of alloys, which include, but are not limited to, in addition to magnesium as the main constituent, additives (usually up to approximately 10%) of aluminum, manganese, zinc, copper, nickel, cerium mixed metal and other rare earth metals, silver, zirconium, silicon, combinations thereof and the like. Magnesium alloys are divided into Mg wrought alloys (usually, but not exclusively, based on Mg—Mn, Mg—Al—Zn) and Mg cast alloys. The MG cast alloys are divided into sand casting, chill casting and die casting according to the alloy constituents. Magnesium alloys can be processed by most known primary forming methods and reshaping methods.

The alloy additives determine the properties of the metallic material to a significant extent. For example, it is known that an aluminum content of more than approximately 10 weight-percent leads to embrittlement of the alloys. Zinc, and especially zirconium, increases the toughness, whereas manganese improves the corrosion resistance. Beryllium additives in the amount of a few ppm will significantly reduce the oxidation tendency of the molten metal but beryllium additives are undesirable because of their toxicity. Rare earth metals and thorium increase the high-temperature strength. The melting point of the alloys is usually between 590° C. and 650° C.

The main areas of use of magnesium alloys include aviation, mechanical engineering of all types, optical equipment, electrical engineering, electronics, conveyance means, office machines and household appliances, and in areas where strength and rigidity with the lowest possible weight are important, while also achieving low manufacturing costs in large series. Magnesium alloys are becoming increasingly important in automotive engine construction. A special application relates to the use of biodegradable magnesium alloys in medical technology, in particular, for vascular and orthopedic implants.

One limit of known magnesium alloys is the ductility of the material, which is often inadequate for certain processing methods and intended purposes. One approach to improve ductility might be to reduce the grain size of the metallic structure (refining). Refining includes all metallurgical measures that lead to a small grain size of an alloy. In general, this presupposes increasing the seed count in the melt in solidification or in the solid state by finely dispersed precipitates. Refining has an advantageous effect on the mechanical properties, in particular, the ductility of the alloy. In the field of magnesium alloys, very small grain sizes have previously been achieved only on a small scale preparatively, e.g., by ECAP/ECAE methods (ECAP stands for equal channel angular pressing; ECAE stands for equal channel angular extrusion). However, the aforementioned methods cannot be implemented on a large scale industrially; so far only small volumes (a few $cm^3$) of extremely fine-grained alloys have been produced, primarily with the industrial magnesium alloy AZ31. So far, there has been only inadequate information of a generally valid nature about the alloy components required for refining or even their amounts in magnesium alloys.

There is, therefore, an ongoing demand for magnesium alloys that allow refining even with access to traditional large-scale industrial methods. In addition, there is a demand for a magnesium alloy having a reduced grain size in comparison with traditional alloys with regard to improved ductility. Furthermore, there is a demand for a production method for a fine-grained magnesium alloy that can be implemented technically on a large scale. Finally, from the standpoint of ecological aspects as well as technical medical use of the alloys, it is necessary to select the alloy components based on toxicological and/or biocompatible factors; biocompatible factors are important, in particular, to avoid the aluminum that is present in many magnesium alloys.

SUMMARY

The present disclosure provides several exemplary embodiments of the present invention, some of which are discussed below.

One aspect of the present disclosure provides a magnesium alloy, comprising Y: 0.5-10 weight-percent, Zn: 0.5-6 weight-percent, Ca: 0.05-1 weight-percent, Mn: 0-0.5 weight-percent, Ag: 0-1 weight-percent, Ce: 0-1 weight-percent, Zr: 0-1 weight-percent or Si: 0-0.4 weight-percent, wherein the amounts are based on weight-percent of the alloy and Mg and manufacturing-related impurities constitute the remainder of the alloy to a total of 100 weight-percent.

Another aspect of the present disclosure provides a method for manufacturing a fine-grained magnesium alloy, comprising the steps of (a) preparing a mixture comprising Y: 0.5-10 weight-percent, Zn: 0.5-6 weight-percent, Ca: 0.05-1 weight-percent, Mn: 0-0.5 weight-percent, Ag: 0-1 weight-percent, Ce: 0-1 weight-percent, Zr: 0-1 weight-percent, or Si: 0-0.4 weight-percent, wherein the amounts are based on weight-percent of the mixture, Mg and manufacturing-related impurities constituting the remainder of the mixture to a total of 100 weight-percent; (b) primary forming a magnesium alloy from the mixture by casting; and (c) reshaping the magnesium alloy by compressing.

A further aspect of the present disclosure provides a magnesium alloy produced by a method comprising manufacturing a fine-grained magnesium alloy, comprising the steps of (a) preparing a mixture comprising Y: 0.5-10 weight-percent, Zn: 0.5-6 weight-percent, Ca: 0.05-1 weight-percent, Mn: 0-0.5 weight-percent, Ag: 0-1 weight-percent, Ce: 0-1 weight-percent, Zr: 0-1 weight-percent, or Si: 0-0.4 weight-percent, wherein the amounts are based on weight-percent of the mixture, Mg and manufacturing-related impurities constituting the remainder of the mixture to a total of 100 weight-percent; (b) primary forming a magnesium alloy from the mixture by casting; and (c) reshaping the magnesium alloy by compressing.

An additional aspect of the present disclosure provides a method of producing a biodegradable implant, comprising (a) producing a magnesium alloy by a process, the magnesium alloy comprising Y: 0.5-10 weight-percent, Zn: 0.5-6 weight-percent, Ca: 0.05-1 weight-percent, Mn: 0-0.5 weight-percent, Ag: 0-1 weight-percent, Ce: 0-1 weight-percent, Zr: 0-1 weight-percent or Si: 0-0.4 weight-percent, wherein the amounts are based on weight-percent of the alloy and Mg and manufacturing-related impurities constitute the remainder of the alloy to a total of 100 weight-percent; and (b) forming a biodegradable implant incorporating the magnesium alloy of step (a).

Yet another aspect of the present disclosure provides a method of producing a biodegradable implant, comprising (a) producing a magnesium alloy by a process comprising a method for manufacturing a fine-grained magnesium alloy, comprising the steps of (i) preparing a mixture comprising Y: 0.5-10 weight-percent, Zn: 0.5-6 weight-percent, Ca: 0.05-1 weight-percent, Mn: 0-0.5 weight-percent, Ag: 0-1 weight-percent, Ce: 0-1 weight-percent, Zr: 0-1 weight-percent, or Si: 0-0.4 weight-percent, wherein the amounts are based on weight-percent of the mixture, Mg and manufacturing-related impurities constituting the remainder of the mixture to a total of 100 weight-percent; (ii) primary forming a magnesium alloy from the mixture by casting; and (iii) reshaping the magnesium alloy by compressing; and (b) forming a biodegradable implant incorporating the magnesium alloy of step (a).

DETAILED DESCRIPTION

A first exemplary embodiment relates to a magnesium alloy having the composition:

| | |
|---|---|
| Y: | 0.5-10 |
| Zn: | 0.5-6 |
| Ca: | 0.05-1 |
| Mn: | 0-0.5 |
| Ag: | 0-1 |
| Ce: | 0-1 |
| Zr: | 0-1 or Si: 0-0.4 | wherein the amounts are based on weight-percent of the alloy and Mg and manufacturing-related impurities constitute the remainder of the alloy to a total of 100 weight-percent. The alloy is characterized in that, with a suitable treatment, it can be converted to a very fine-grained structure (in particular with grain sizes less than about 20 µm). Furthermore, the alloy components have little or no toxicological relevance, so that a technical medical application seems virtually predestined. The amount of Mn is preferably in the range of 0.05 to 0.5 weight-percent.

The present disclosure is based on the finding that, among other things, the alloy elements in the amounts indicated are able to inhibit grain growth, first in solidification from the melt, due to their accumulation at the solidification front, and second, in hot forming due to the formation of intermetallic phases. In the case of a coarse-grained structure, plastic forming is dominated by displacement movements on the basal plane and by twinning; however, a fine-grained magnesium structure allows the activation of prism and pyramidal slippage even at room temperature, which greatly improves the ductility of the material. The alloy elements with a high Q factor (grain growth restriction factor) that accumulate at the solidification front during solidification delay the grain growth and thus contribute toward a low grain size of the cast structure. The very small intermetallic phases present in the solidified magnesium alloy and having the composition to be explained in greater detail below influence recrystallization in hot forming of the cast structure and also make a significant contribution toward refining of the structure. The presence of intermetallic phases not only improves the ductility of a material but also has a significant influence on its corrosion properties. The latter is important, in particular, when the magnesium alloy is used to produce biodegradable implants (preferably stents). As a rule, the presence of fine intermetallic phases (instead of coarse-grained phases) with a special stoichiometric ratio will reduce the corrosion resistance. The goal is to produce an approximately monophasic structure and avoid a coarse polyphasic structure.

Preferred magnesium alloys are obtained by the following restrictions on the amounts of the stated alloy constituents or several of these alloy constituents (amounts in weight-percent):

| | |
|---|---|
| Y: | 0.5-4; |
| Zn: | 0.5-3.0; in particular 0.8-2.5; |
| Ca: | 0.05-0.3; in particular 0.05-0.2; |
| Mn: | 0-0.25; in particular 0.05-0.25; |
| Ag: | 0.05-0.6; |
| Ce: | 0-0.5; |
| Zr: | 0-0.7; in particular 0.3-0.7 or Si: 0-0.25; in particular 0.05-0.25. |

According to preliminary experiments and theoretical considerations, the alloy compositions appear to be especially suitable for extremely fine-grained magnesium-based materials (in particular with grain sizes of less than about 20 µm). It should be pointed out that zirconium and silicon preferably should not be used together, because intermetallic phases that are unsuitable for the purposes of refining are formed from the two elements.

For purposes of the present disclosure, the term "alloy," in the inventive sense, refers to a monophasic or polyphasic metallic material of a binary or polynary system, the starting components (alloy elements) of which enter into metallurgical interactions with one another and thereby lead to the formation of new phases (mixed crystals, intermetallic compounds, superlattice). A magnesium alloy contains magnesium as the main constituent.

It is preferable, in particular in conjunction with the aforementioned preferred variants of the composition of the magnesium alloy, for the magnesium alloy to contain one or more intermetallic phases, consisting of:
(i) Mg and one or more elements selected from the group consisting of: Zn, Ca, Mn, Ag, Ce, Zr, Si and Y; or
(ii) 2 or more elements selected from the group consisting of: Zn, Ca, Mn, Ag, Ce, Zr, Si and Y.

The presence of one or more intermetallic phases of the aforementioned compositions is an important indication of the suitability of the alloy for production of a fine-grained material (preferably with a grain size of less than about 20 µm), if this alloy is not already in the form of a fine-grained material. Especially preferably, one or more intermetallic phases selected from the following group is present: $Ca_2Mg_6Zn_3$, $AgMg_4$, $Mn_2Zr$, $ZnZr$, $Zn_2Zr$, $MgZn$, $MgZn_2$, $Mg_2Si$, $Mg_3Y_2Zn_3$, $Mg_3YZn_6$, $Mg_{12}YZn$ and $Mg_{24}Y_5$.

Intermetallic phases (compounds) are chemical compounds of two or more metallic elements present in the structure of alloys, and their structure differs significantly from that of the metals forming them. In addition to cubic structures, there are also tetragonal and more complex structures. In addition to metallic bonds, the lattice also contains atomic and ionic bonds. In addition to intermetallic phases with a stoichiometric composition according to the prevailing valences, there are those in which this precise composition represents only a special case in a broad range of homogeneity. This follows from the tendency of the metals involved to develop a lattice having the highest possible coordination number and packing density at the given bond ratios. Metal bonding and properties are more pronounced, the higher the coordination number, e.g., in the group of Laves phases. Hume-Rothery phases form broad homogeneity ranges, as do intermetallic phases having interstitial structures. In the growth of the homopolar (covalent) and polar bond components, the intermetallic phases crystallize in lattices having a low coordination number, e.g., Zintl phases. The melting points of the intermetallic phases are much higher than the melting points of the metal components; the electric conductivity of the intermetallic phases is much lower than the electric conductivity of the metal components. In the finely dispersed form, intermetallic compounds occurring as phases in metallic structures may increase the strength or, in a coarser form, may lead to embrittlement of the alloy the intermetallic compounds occurring as phases in metallic structures may also have a negative effect on the corrosion resistance.

The volume amount of the magnesium alloy in the intermetallic phases is preferably less than about 3 volume-percent, in particular less than about 2 volume-percent, especially preferably less than about 1 volume-percent, in particular in conjunction with the variant of the embodiment described above. Also preferred as an alternative or in addition:

(i) a grain size of the intermetallic phases less than about 3 µm, in particular less than about 1 µm; and
(ii) a grain size of the alloy less than about 20 µm, in particular less than about 10 µm.

For purposes of the present disclosure, the term "grain size" refers to the average diameter of the crystallites present in a metallographic micrograph.

The magnesium alloys in the exemplary embodiments described above have especially favorable properties for processing and for their later intended purpose in comparison with traditional magnesium alloys: the ductility of the magnesium alloys is greatly elevated. For purposes of the present disclosure, the term "ductility" (or toughness, deformation capacity) refers to the ability of a metallic material to undergo permanent deformation under sufficiently high mechanical loads before cracking occurs. This ability is of great importance for many construction parts because only a ductile material is capable of dissipating local mechanical stress peaks by undergoing permanent deformation without cracking and with simultaneous cold solidification. This aspect, in particular, makes it especially advantageous to use the inventive magnesium alloys as a material, for example, for biodegradable implants, in particular, stents. With a given material, the ductility depends on the temperature, the stress rate, the multi-axle character of the acting mechanical stress state and the environment. Characteristic values of ductility include, e.g., the elongation at break and necking, the notched impact strength and the fracture toughness.

The disclosed magnesium alloy preferably has a greater than about 20% elongation at break of A5 standard specimens at room temperature. For purposes of the present disclosure, elongation at break (elongation at break, formula notation $\epsilon_R$ or $A_5$) is the percentage ratio of the change in length $\Delta L$ (at the moment of breaking) under a tensile strength to the starting length $L_0$.

A second exemplary embodiment relates to a method for manufacturing a fine-grained magnesium alloy. One exemplary method provides the steps of:

(i) Preparing a mixture having the composition:

| | |
|---|---|
| Y: | 0.5-10 |
| Zn: | 0.5-6 |
| Ca: | 0.05-1 |
| Mn: | 0-0.5 |
| Ag: | 0-1 |
| Ce: | 0-1 |
| Zr: | 0-1 or Si: 0-0.4 | where the amounts are based on weight-percent of the mixture, Mg and manufacturing-related impurities constituting the remainder of the mixture to a total of 100 weight-percent;
(ii) Primary forming of a magnesium alloy from the mixture by casting; and
(iii) Reshaping the magnesium alloy by compressing.

By means of the disclosed method, it is possible for the first time to produce very fine-grained magnesium alloys on an industrial scale. It is possible to rely on empirical values from essentially known metallurgical methods and thus the development of an industrial manufacturing process is greatly simplified. Primary forming in step (ii) is especially preferably performed by strand casting, because this method leads to materials having a high homogeneity. Furthermore, it is preferable if the reshaping in step (iii) is performed by extrusion molding, especially at a temperature in the range of 280° C.-420° C., most especially preferably at a temperature in the range of 300° C.-400° C. With regard to the composition of the mixture, the composition of the mixture may optionally have to be adjusted to the same compositions already indicated as preferred in conjunction with the description of the magnesium alloy.

For purposes of the present disclosure, casting relates to a manufacturing method in which materials in a molten or free-flowing state are cast into a prepared hollow mold (casting mold) which forms the negative of the piece to be cast. The materials solidify in the mold and form a positive image of the mold. Solidification proceeds by solidifying the metallic melt. If pressureless casting is not sufficient to fill the mold, filling can be performed under pressure (die casting, injection molding) or by using centrifugal force (spin casting) optionally with additional evacuation of the casting mold (vacuum casting). For purposes of the present disclosure, casting, in the narrower sense, relates to strand casting. In contrast with block casting, strand casting is performed as a continuous process. A bottomless cooled chill mold is used, and the molten metal is cast into this mold. The extruded shell solidifies inside the chill mold and is then removed in the direction of casting and surrounds the molten core. After leaving the chill mold, the extruded shell is cooled further with water until the strand has solidified completely.

For purposes of the present disclosure, reshaping (or shaping) is the conventional term used in metal working for the plastic deformation of a metal semi-finished product under the influence of mechanical forces. For purposes of the present disclosure, compressing means primarily compression and shaping of solids, in particular, reshaping of materials without cutting by applying pressure, usually in hydraulically-operated machines. For purposes of the present disclosure, the term "extrusion molding" refers to a compression method in which a metal billet is forced through a female mold by a ram. The billet is surrounded by a recipient. The outer shape of the pressed strand is determined by the female mold. Cavities can also be produced by introducing mandrels of various shapes. Wires, tubes and profiles can be produced by extrusion molding.

A third exemplary embodiment is directed at a magnesium alloy produced by the method described above.

A fourth exemplary embodiment is the use of a magnesium alloy produced by this method or a fine-grained magnesium alloy produced by some other method having the preferred structural properties in medical technology as mentioned above, in particular, for production of a biodegradable implant. The biodegradable implant is preferably a stent. The present disclosure also provides a method for producing a biodegradable implant using the magnesium alloy produced by a method provided in the present disclosure.

EXAMPLES

Example 1

A mixture having the composition (in weight-percent):

| Y: | 3.5 |
|---|---|
| Zn: | 0.85 |
| Ca: | 0.25 |
| Ag: | 0.5 |
| Mn: | 0.15 |
| remainder: | Mg and production-related impurities | is melted at 700° C. in a crucible under a protective atmosphere and cast in a cylindrical mold with a diameter of 25 mm. The cast piece with a grain size of approximately 150 micrometers is then heated to 300° C. and extruded through a female mold to a diameter of 5 mm (extrusion ratio 25). The grain size thereby achieved amounts to approximately 10 micrometers. The present intermetallic phases include those of the types $Ca_2Mg_6Zn_3$, $Mg_3Y_2Zn_3$, $Mg_3YZn_6$ and $AgMg_4$ with an average size of less than about 3 micrometers and a total amount of less than about 3 volume-percent. The ductility thereby achieved, measured in percentage elongation at break, is 24%; the strength (tensile strength) is found to be 270 MPa.

Example 2

Magnesium alloy having the composition (in weight-percent):

| Y: | 6.5 |
|---|---|
| Zn: | 1.5 |
| Ca: | 0.25 |
| Ag: | 0.5 |
| Mn: | 0.15 |
| Zr: | 0.5 |
| Remainder: | Mg and production-related impurities | is melted at 700° C. in a crucible under a protective atmosphere and cast in a cylindrical mold with a diameter of 25 mm. The cast piece with a grain size of approximately 50 micrometers is then heated to 300° C. and extruded through a female mold to a diameter of 5 mm (extrusion ratio 25). The resulting grain size is approximately 4 micrometers. The present intermetallic phases are primarily of the types $Ca_2Mg_6Zn_3$, $AgMg_4$ and $Zn_2Zr$ with an average size of less than about 1 micrometer and a total amount of less than about 1 volume-percent. The resulting ductility, measured as percentage elongation at break, is 26%, and the strength (yield point) is 190 MPa.

Example 3

A magnesium alloy having the composition (in weight-percent):

| Y: | 0.8 |
|---|---|
| Zn: | 2.0 |
| Ca: | 0.25 |
| Mn: | 0.15 |
| remainder: | Mg and production-related impurities | was melted at 690° C. in a magnesium furnace under a protective atmosphere and strand-cast in cylindrical pressed billets with a diameter of 180 mm with water cooling. Pressed billets with a grain size of approximately 200 micrometers were then heated to 360° C. and extruded through a female mold to a diameter of 20 mm (extrusion ratio 30). The resulting grain size was approximately 7 micrometers. The intermetallic phases included those of the types $Ca_2Mg_6Zn_3$, $Mg_3Y_2Zn_3$ and $Mg_3YZn_6$ with an average size of less than about 3 micrometers and a total amount of less than about 3 volume-percent. The resulting ductility, measured as percentage elongation at break, was 28%, and the strength (tensile strength) was found to be 260 MPa.

Example 4

A mixture having the composition (in weight-percent):

| Y: | 2.0 |
|---|---|
| Zn: | 0.9 |
| Ca: | 0.25 |
| Mn: | 0.15 |
| remainder: | Mg and production-related impurities | was melted at 690° C. in a magnesium furnace under a protective atmosphere and strand-cast in cylindrical pressed billets with a diameter of 180 mm with water cooling (according to the disclosed method, second aspect, (ii) primary forming). Pressed billets with a grain size of approximately 250 micrometers were then heated to 380° C. and extruded through a female mold to a diameter of 20 mm (extrusion ratio 30, according to the disclosed method, second aspect, (iii) reshaping). The resulting grain size was approximately 11 micrometers. The present intermetallic phases include those of the types $Ca_2Mg_6Zn_3$, $Mg_3Y_2Zn_3$ and $Mg_3YZn_6$ with an average size of less than about 3 micrometers and a total amount of less than about 3 volume-percent. The resulting ductility, measured as percentage elongation at break, was 28%, and the strength (tensile strength) was found to be 250 MPa.

Example 5

A mixture having the composition (in weight-percent):

| Y: | 2.0 |
|---|---|
| Zn: | 0.9 |

-continued

| Ca: | 0.25 |
| Mn: | 0.15 |
| Zr: | 0.5 |
| remainder: | Mg and production-related impurities | was melted at 690° C. in a magnesium furnace under a protective atmosphere and strand-cast in cylindrical pressed billets with a diameter of 180 mm with water cooling (according to the disclosed method, second aspect, (ii) primary forming). Pressed billets with a grain size of approximately 120 micrometers were then heated to 400° C. and extruded through a female mold to a diameter of 20 mm (extrusion ratio 30, according to the disclosed method, second aspect, (iii) reshaping). The resulting grain size was approximately 5 micrometers. The present intermetallic phases include those of the types $Ca_2Mg_6Zn_3$, $Mg_3Y_2Zn_3$, $Mg_3YZn_6$, $Zn_2Zr$ and $Mn_2Zr$ with an average size of less than about 3 micrometers and a total amount of less than about 3 volume-percent. The resulting ductility, measured as percentage elongation at break, was 22%, and the strength (tensile strength) was found to be 300 MPa.

What is claimed is:

1. A magnesium alloy, consisting of:

| Y: | 0.5-10 weight-percent, |
| Zn: | 0.5-6 weight-percent, |
| Ca: | 0.05-1 weight-percent, |
| Mn: | 0-0.5 weight-percent, |
| Ag: | 0-1 weight-percent, |
| Ce: | 0-1 weight-percent, |
| Zr: | 0-1 weight-percent or |
| | Si: 0-0.4 weight-percent, | wherein the amounts are based on weight-percent of the alloy and Mg and manufacturing-related impurities constitute the remainder of the alloy to a total of 100 weight-percent,
wherein the magnesium alloy has a monophasic structure,
wherein the magnesium alloy has an effective amount of one or more intermetallic phases having a volume amount of less than about 3 vol. % to produce an alloy having a grain size of less than about 20 μm, and
wherein the grain size of the intermetallic phases is less than about 3 μm.

2. The magnesium alloy of claim 1, wherein the magnesium alloy comprises one or more intermetallic phases comprising:
   (a) Mg and one or more elements selected from the group consisting of Zn, Ca, Mn, Ag, Ce, Zr, Si and Y; or
   (b) two or more elements selected from the group consisting of Zn, Ca, Mn, Ag, Ce, Zr, Si and Y.

3. The magnesium alloy of claim 2, comprising one or more intermetallic phases selected from the group consisting of $Ca_2Mg_6Zn_3$, $AgMg_4$, $Mn_2Zr$, $ZnZr$, $Zn_2Zr$, $MgZn$, $MgZn_2$, $Mg_2Si$, $Mg_3Y_2Zn_3$, $Mg_3YZn_6$, $Mg_{12}YZn$ and $Mg_{24}Y_5$.

4. The magnesium alloy of claim 1, wherein the amount by volume of the magnesium alloy in the intermetallic phases is less than about 2 volume-percent.

5. The magnesium alloy of claim 1, wherein the grain size of the alloy is less than about 10 μm.

6. The magnesium alloy of claim 1, wherein Y is: 0.5-4 weight-percent.

7. The magnesium alloy of claim 1, wherein Zn is: 0.5-3.0 weight-percent.

8. The magnesium alloy of claim 1, wherein Mn is: 0-0.25 weight-percent.

9. The magnesium alloy of claim 1, wherein Ag is: 0.05-0.6 weight-percent.

10. The magnesium alloy of claim 1, wherein Ce is: 0-0.5 weight-percent.

11. The magnesium alloy of claim 1, wherein Zr is: 0.3-0.7 weight-percent.

12. The magnesium alloy of claim 1, wherein Si is: 0-0.25 weight-percent.

13. A magnesium alloy produced by a method, comprising:
    (a) preparing a mixture consisting of:

| Y: | 0.5-10 weight-percent, |
| Zn: | 0.5-6 weight-percent, |
| Ca: | 0.05-0.3 weight-percent, |
| Mn: | 0-0.5 weight-percent, |
| Ag: | 0-1 weight-percent, |
| Ce: | 0-1 weight-percent, |
| Zr: | 0-1 weight-percent, or Si: 0-0.4 weight-percent, | wherein the amounts are based on weight-percent of the mixture, Mg and manufacturing-related impurities constituting the remainder of the mixture to a total of 100 weight-percent;
    (b) forming a magnesium alloy by casting the mixture of step a); and
    (c) reshaping the magnesium alloy by compressing the casting of step b),
wherein the magnesium alloy has a monophasic structure,
wherein the magnesium alloy has and effective amount of one or more intermetallic phases having a volume amount of less than about 3 vol. % to produce an alloy having a grain size of less than about 20 μm, and
wherein the grain size of the intermetallic phases is less than about 3 μm.

* * * * *